US011779594B2

(12) United States Patent
Terruzzi

(10) Patent No.: US 11,779,594 B2
(45) Date of Patent: Oct. 10, 2023

(54) COMPOSITIONS FOR THE TREATMENT OF EPITHELIAL LESIONS

(71) Applicant: INTERNATIONAL HEALTH SCIENCE S.R.L., Lissone (IT)

(72) Inventor: Carlo Terruzzi, Caglio (IT)

(73) Assignee: INTERNATIONAL HEALTH SCIENCE S.R.L., Lissone (IT)

( * ) Notice: Subject to any disclaimer, the term of this patent is extended or adjusted under 35 U.S.C. 154(b) by 0 days.

(21) Appl. No.: 17/770,536

(22) PCT Filed: Oct. 22, 2020

(86) PCT No.: PCT/EP2020/079757
§ 371 (c)(1),
(2) Date: Apr. 20, 2022

(87) PCT Pub. No.: WO2021/078864
PCT Pub. Date: Apr. 29, 2021

(65) Prior Publication Data
US 2022/0409654 A1 Dec. 29, 2022

(30) Foreign Application Priority Data
Oct. 22, 2019 (EP) .................................... 19204604

(51) Int. Cl.
| A61K 31/728 | (2006.01) |
| A61P 17/02 | (2006.01) |
| A61P 1/04 | (2006.01) |
| A61K 9/00 | (2006.01) |
| A61K 9/06 | (2006.01) |
| A61K 9/16 | (2006.01) |
| A61K 31/198 | (2006.01) |
| A61K 31/401 | (2006.01) |
| A61K 31/77 | (2006.01) |
| A61K 31/78 | (2006.01) |
| A61K 36/899 | (2006.01) |

(52) U.S. Cl.
CPC .......... *A61K 31/728* (2013.01); *A61K 9/0056* (2013.01); *A61K 9/06* (2013.01); *A61K 9/16* (2013.01); *A61K 31/198* (2013.01); *A61K 31/401* (2013.01); *A61K 31/77* (2013.01); *A61K 31/78* (2013.01); *A61K 36/899* (2013.01); *A61P 1/04* (2018.01); *A61P 17/02* (2018.01)

(58) Field of Classification Search
CPC ...... A61K 9/0053–0065; A61K 31/198; A61K 31/401; A61K 31/728; A61K 31/77; A61K 31/78; A61K 36/899; A61P 1/04; A61P 17/02–10
See application file for complete search history.

(56) References Cited

FOREIGN PATENT DOCUMENTS

WO 2013001449 A1 1/2013

OTHER PUBLICATIONS

Romeo, U. et al "Oral soft tissue wound healing after laser surgery . . . " Photomed. Laser Surg., vol. 32, No. 1, pp. 10-16. (Year: 2014).*
Palungwachira, P. et al "Antioxidant and anti-inflammatory properties of anthocyanins . . . " Oxid. Med. Cell. Longev., pp. 1-18. (Year: 2019).*
Limsitthichaikoon S, et al "Topical oral wound healing potential of anthocyanin complex . . . " Therapeutic Delivery, vol. 9, No. 5, pp. 359-374. (Year: 2018).*
Jones, D. et al "Rheological, mechanical and mucoadhesive properties . . . " Int. J. Pharm., vo 372, pp. 49-58. (Year: 2009).*
Mariggio, M. et al "Enhancement of fibroblast proliferation . . . " Int. J. Immunopath. Pharmacol., vol. 22, No. 2, pp. 485-492. (Year: 2009 ).*
Carvalho, F. et al "Rheological, mechanical, and bioadhesive behavior . . . " Drug Dev. Ind. Pharm., vol. 39, No. 11, pp. 1750-1757. (Year: 2013).*
Song, J. et al "Oxidative stress from reflux esophagitis . . . " Free Rad. Res., vol. 50, No. 10, pp. 1071-1079. (Year: 2016).*
Agostinis C. et al., "Protective and regenerative effects of a novel medical device against esophageal mucosal damage using in vitro and ex vivo models", Biomedicine and Pharmacotherapy, vol. 131, Sep. 19, 2020.
Favia G. et al., "Accelerated wound healing of oral soft tissues and angiogenic effect induced by a pool of aminoacids combined to sodium hyaluronate (AMINOGAM (R))", Journal of Biological Regulators and Homeostatic Agents, vol. 22, No. 2, Apr. 2008, pp. 109-116.
International Preliminary Report on Patentability of PCT/EP2020/079757 dated Oct. 21, 2021.
Search Report and Written Opinion of PCT/EP2020/079757 dated Feb. 11, 2021.

(Continued)

*Primary Examiner* — Leigh C Maier
(74) *Attorney, Agent, or Firm* — SILVIA SALVADORI, P.C.; Silvia Salvadori

(57) ABSTRACT

The present invention concerns the field of medications for the treatment of lesions and wounds of the skin and mucosa. The present invention relates to the use of a composition comprising a combination of a mucoadhesive component in the range from 0.05-20% by weight, an emollient component in the range from 0.02-20% by weight, hydrating and mucoprotective component i.e. hyaluronic acid in the range from 0.01-15% by weight and epithelizing component i.e. one or more amino acids in the range from 0.02-5% by weight in the treatment of epithelial lesions. The invention further comprises a composition comprising: —carbomer (poly acrylic acid) in the range from 0.05% to 5%; —sodium hyaluronate in the range from 0.01% to 15%; —poloxamer (copolymers of ethylene oxide and propylene oxide) in the range from 0.1% to 15%; —*Oryza sativa* extract in the range from 0.2% to 20%; and —one or more amino acids in the range from 0.025% to 5%, wherein said percentages are by weight of the total weight of the product (w/w).

9 Claims, 11 Drawing Sheets

(56) References Cited

OTHER PUBLICATIONS

Tamotsu Matsuhashi et al., "Protective effect of a novel rice extract against ethanol-induced gastric mucosal injury in rat", Digestive Diseases and Sciences, vol. 52, No. 1, Jan. 11, 2007, pp. 434-441.

Trinovita et al., "Potential gastroprotective activity of rice bran (*Oryza sativa* L.) extracted by ionic liquid-microwave-assisted extraction against ethanol-induced acute gastric ulcers in rat model", Scientia Pharmaceutica, vol. 86, No. 3, Sep. 7, 2018, p. 35.

* cited by examiner

Statistical significance: *P<0.05 vs untreated cells; #P<0.01 vs placebo.

Statistical significance: *P<0.05 vs untreated cells; #P<0.05 vs placebo.

\*\*\* P<0.0001 for Invention vs placebo;

\*\* P<0.01 for Invention at Day 14 (end of treatment) vs Day 7 (interim).

*** P<0.0001 for our invention vs placebo

COMPOSITIONS FOR THE TREATMENT OF EPITHELIAL LESIONS

This application is a U.S. national stage of PCT/EP2020/079757 filed on 22 Oct. 2020, which claims priority to and the benefit of European Application No. 19204604.3 filed on 22 Oct. 2019, the contents of which are incorporated herein by reference in their entireties.

FIELD OF THE INVENTION

The present invention concerns the field of medications for the treatment of lesions and wounds of the skin and mucosa.

The present invention relates to the use of a composition comprising a combination of a mucoadhesive component in the range from 0.05-20% by weight, an emollient component in the range from 0.02-20% by weight, hydrating and mucoprotective component i.e. hyaluronic acid in the range from 0.01-15% by weight and epithelizing component i.e. one or more amino acids in the range from 0.02-5% by weight in the treatment of epithelial lesions.

The invention further comprises a composition comprising:
- carbomer (poly acrylic acid) in the range from 0.05% to 5%;
- sodium hyaluronate in the range from 0.01% to 15%;
- poloxamer (copolymers of ethylene oxide and propylene oxide) in the range from 0.1% to 15%;
- *Oryza sativa* extract in the range from 0.2% to 20%; and
- one or more amino acids in the range from 0.025% to 5%, wherein said percentages are by weight of the total weight of the product (w/w).

STATE OF THE ART

Epithelial tissues are specialized to protect underlying tissues from environmental influences such as physical and chemical agents, infection by invasive microorganisms as well as water and heat loss. They are grouped into simple, transitional and stratified epithelia, which line the cavities and surfaces of structures throughout the body, and also form glands, separate compartments, regulate the exchange of molecules and act as sensory organs. Stratified epithelia such as the epidermis and oral mucosa are in constant renewal, with cells proliferating in the lower layers, while the intermediate stratum and outermost layers undergo a tissue-specific process of differentiation to form a protective cornified barrier.

A wound results from the breakdown of the epithelial layer integrity, which can happen in several anatomical zones like skin, oral mucosa, esophageal mucosa, etc . . . . Any tissue injury with anatomical integrity disruption with functional loss can be described as a wound. Wound healing mostly means healing of the damaged tissue. The wound healing begins immediately after an injury and represents a complex and dynamic biological process, which includes 3 different phases: inflammation, proliferation, and remodeling. Similarly, numerous growth factors, chemokines, cytokines promote cell proliferation and synthesis of new extracellular matrix (ECM) molecules; this is an important process aimed to restore the matrix microenvironment together with physiological tissue architecture. It is important to note that collagen, one of main components of ECM, is composed of amino acids, mainly glycine and proline, and is produced by numerous cell lines, such as fibroblasts, chondrocytes, osteoblasts, epithelial, and muscular cells.

The greater amount of collagen expresses an acceleration in tissue repair, since collagen is the main structural component in wound healing, being fundamental to the resistance and integrity of all tissues. Experimental studies showed that supplementation of collagen precursor amino acids improved the collagen production and efficiency of tissue repairing processes (Sa et al. 2018). Any disruption leads to abnormal wound healing. Despite the increasing understanding of the biology of healing, the need for the treatment of tissue injuries remains unmet. As a temporary treatment for damaged tissue like skin and mucosa, wound dressings play an important role and are broadly applied to wounds. Although medical dressings and topical treatments have improved considerably over time, more biological functions and better treatment effects are required. In order to be effective, a therapy for wound healing should:

1) Alleviate the inflammatory response by reducing the expression of pro-inflammatory mediators like interleukin (IL)-1, tumor necrosis factor α (TNF-α), and nitric oxide (NO);

2) Support proliferation process in order to expand the granulation tissue, increases the number of new cells and newly formed tissue;

3) Restore the physiological tissue conditions and homeostasis.

Technological advances may contribute to this requirement and have promoted the emergence of various wound treatments.

Gastro-esophageal reflux disease (GERD) is defined as a condition resulting from reflux of stomach contents into the distal and proximal esophagus and causing symptoms or complications. It is due to the involuntary passage of gastric content into the esophagus, without the involvement of both stomach and abdominal muscles, leading to symptoms and injuries of esophageal mucosa.

Symptoms of GERD include: pyrosis (retrosternal burning), dysphagia; reflux of the gastric content into the esophagus. These symptoms are usually increase by the laying position (in fact, often disturb occurs during the night and sleep, according to patients reports).

Extra-esophageal symptoms affect throat and respiratory tract (laryngitis, pharyngitis, chronic cough, hoarseness, dysphonia, asthma).

Often, GERD is associated to esophageal mucosa injuries (esophagitis); chronic irritation of esophageal wall exerted by gastric acids lead first to the mucosal inflammation and later to the lesions and wounds.

GERD treatment includes lifestyle modifications and over-the-counter medications, which include:

Antacids that neutralize stomach acid, which may provide a fast relief. Anyway, antacids alone do not heal the inflamed esophagus damaged by stomach acid. Overuse of some antacids can cause side effects, such as diarrhea or sometimes kidney problems.

Medications to reduce acid production. These medications—known as H-2-receptor blockers—include cimetidine, famotidine, nizatidine and ranitidine. H-2-receptor blockers do not act as quickly as antacids, but they provide longer relief and may decrease acid production from the stomach for up to 12 hours. Stronger versions are available by prescription.

Medications that block acid production and heal the esophagus. These medications—known as proton pump inhibitors—are stronger acid blockers than H-2-receptor blockers and allow time for damaged esophageal tissue to heal. Over-the-counter proton pump inhibitors include lansoprazole and omeprazole.

Although drugs therapy has been a successful treatment for the majority of patients with GERD (especially those with erosive reflux disease), there remains a significant minority of patients (about 30%), who do not respond adequately. There is thus a clinical need for the development of alternative therapies for GERD.

The object of the present invention is therefore the development of a medication for the treatment of lesions and wounds of the skin and mucosa, such as the esophageal mucosa, which does not present the drawbacks that the therapies currently available have.

SUMMARY OF THE INVENTION

The problem underlying the present invention is that of making available compositions capable of treating lesions of the skin and of the mucosa, destined for the management of wound healing.

This problem is resolved by the present finding by the use of specific compositions, comprising specific emollients, which in the combination herein described, stimulate the repairing effect in the tissues.

The present invention concerns a composition comprising a combination of a mucoadhesive component in the range from 0.05-20% by weight, an emollient component in the range from 0.02-20% by weight, hydrating and mucoprotective component i.e. hyaluronic acid in the range from 0.01-15% by weight and epithelizing component i.e. one or more amino acids in the range from 0.02-5% by weight for use in the treatment of epithelial lesions, wherein said emollient component is an extract chosen from the group consisting of *Oryza sativa, Trigonella foenum graecum, Malva sylvestris, Althea officinalis, Matricaria chamomilla, Melissa officinalis, Glycyrrhiza glabra, Calendula officinalis, Vitis vinifera, Borago officinalis, Linum usitatissimum, Opuntia ficus-indica, Prunus dulcis, Aloe barbadensis* and *Avena sativa*.

In a second aspect thereof, this invention moreover provides a composition comprising:
carbomer (poly acrylic acid) in the range from 0.05% to 5%;
sodium hyaluronate in the range from 0.01% to 15%;
poloxamer (copolymers of ethylene oxide and propylene oxide) in the range from 0.1% to 15%;
*Oryza sativa* extract in the range from 0.2% to 20%; and one or more amino acids in the range from 0.025% to 5%,
wherein said percentages are by weight of the total weight of the product (w/w).

BRIEF DESCRIPTION OF THE DRAWINGS

The characteristics and advantages of the present invention will be apparent from the detailed description reported below, from the Examples given for illustrative and non-limiting purposes, and from the annexed FIGS. 1-11, wherein.

Figure 9:
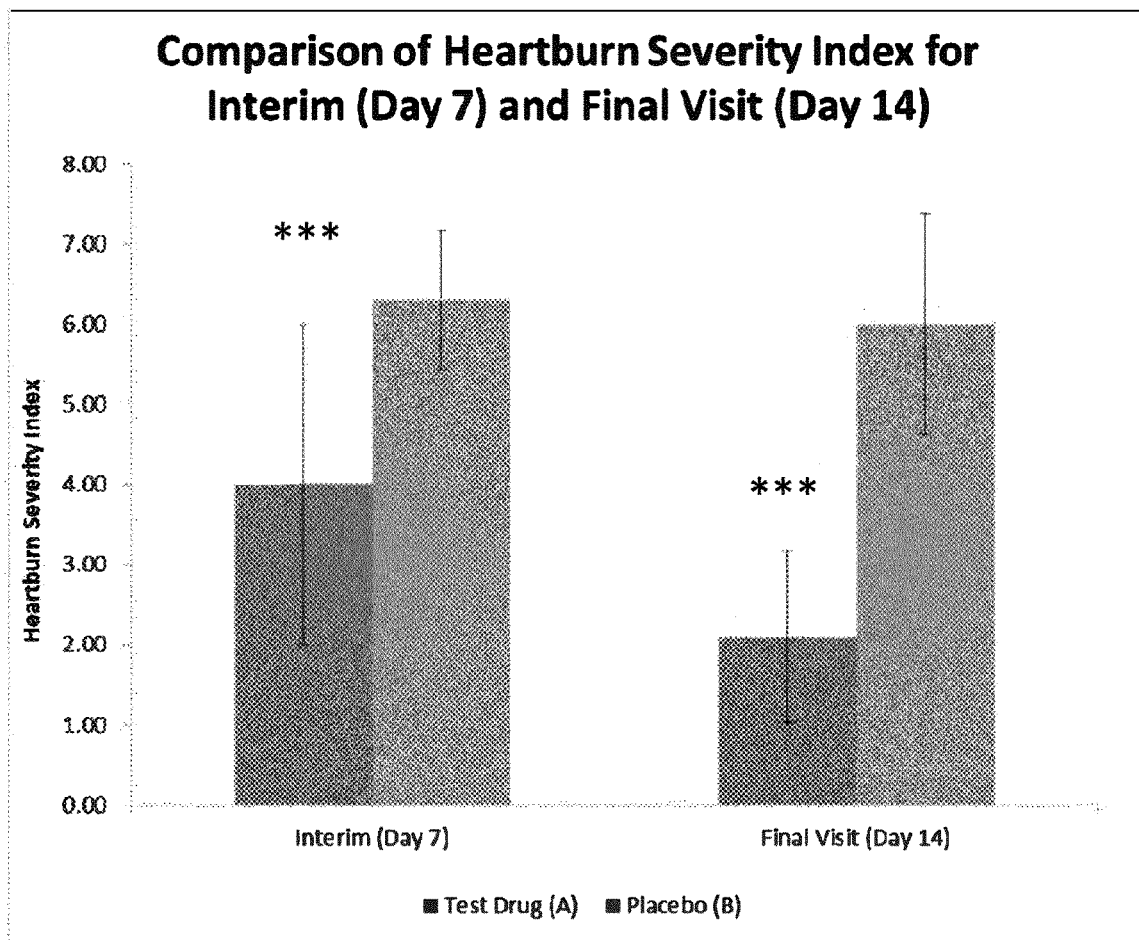

FIG. 9 shows the graph of the heartburn severity index, calculated in the group of patients treated with the composition and with the placebo on day 7 and day 14. ***P<0.0001 for our invention vs placebo. Dark grey: invention; Light grey: placebo.

Figure 10:
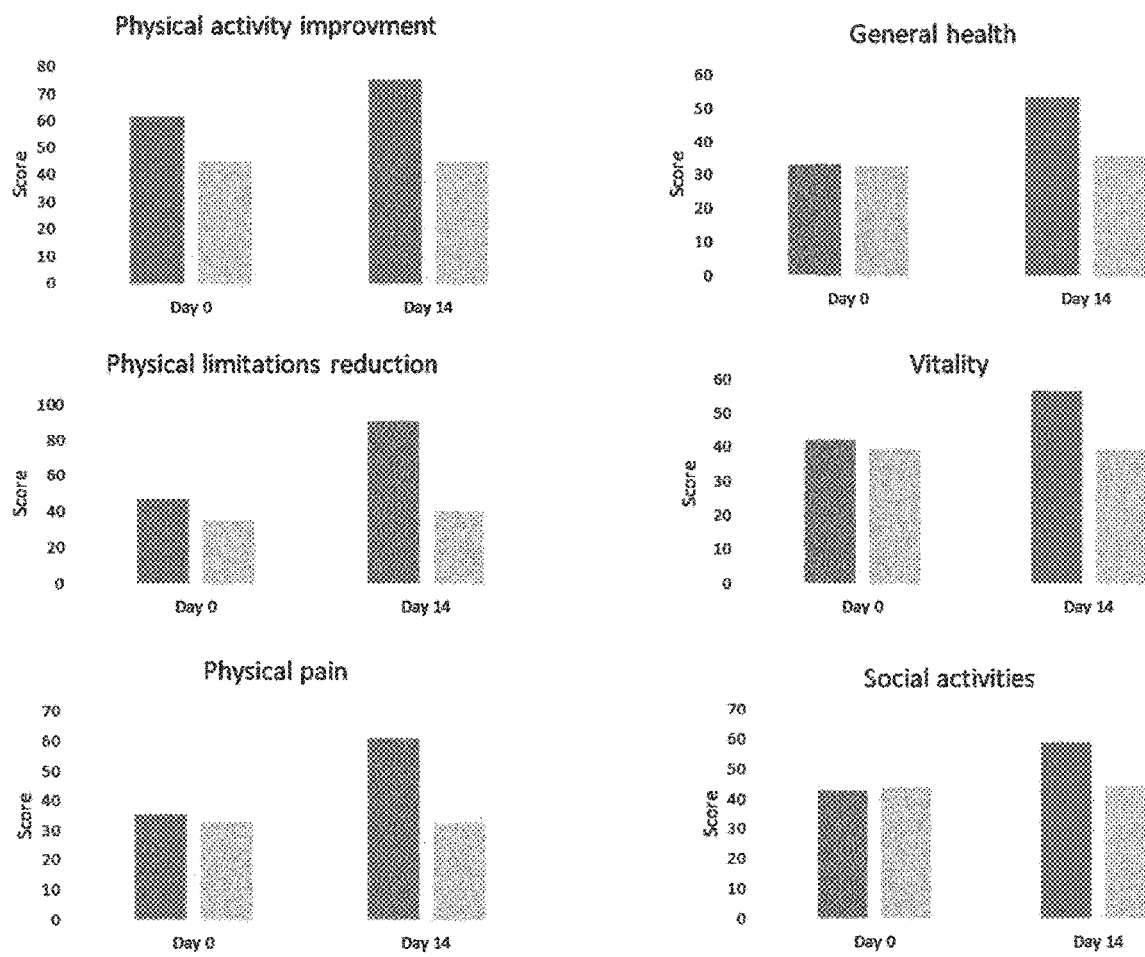
Figure 10:
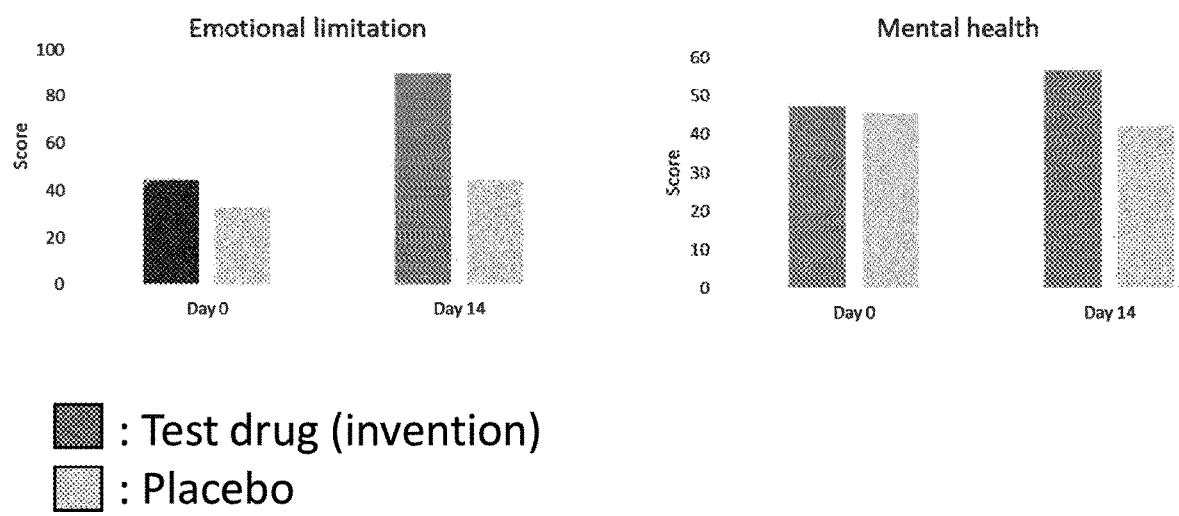

FIG. 10 shows the graphs of the different quality of life, health and well being parameters evaluated for the different patient groups, and assessed by SF-36 questionnaire. Dark grey: invention; Light grey: placebo.

Figure 11:
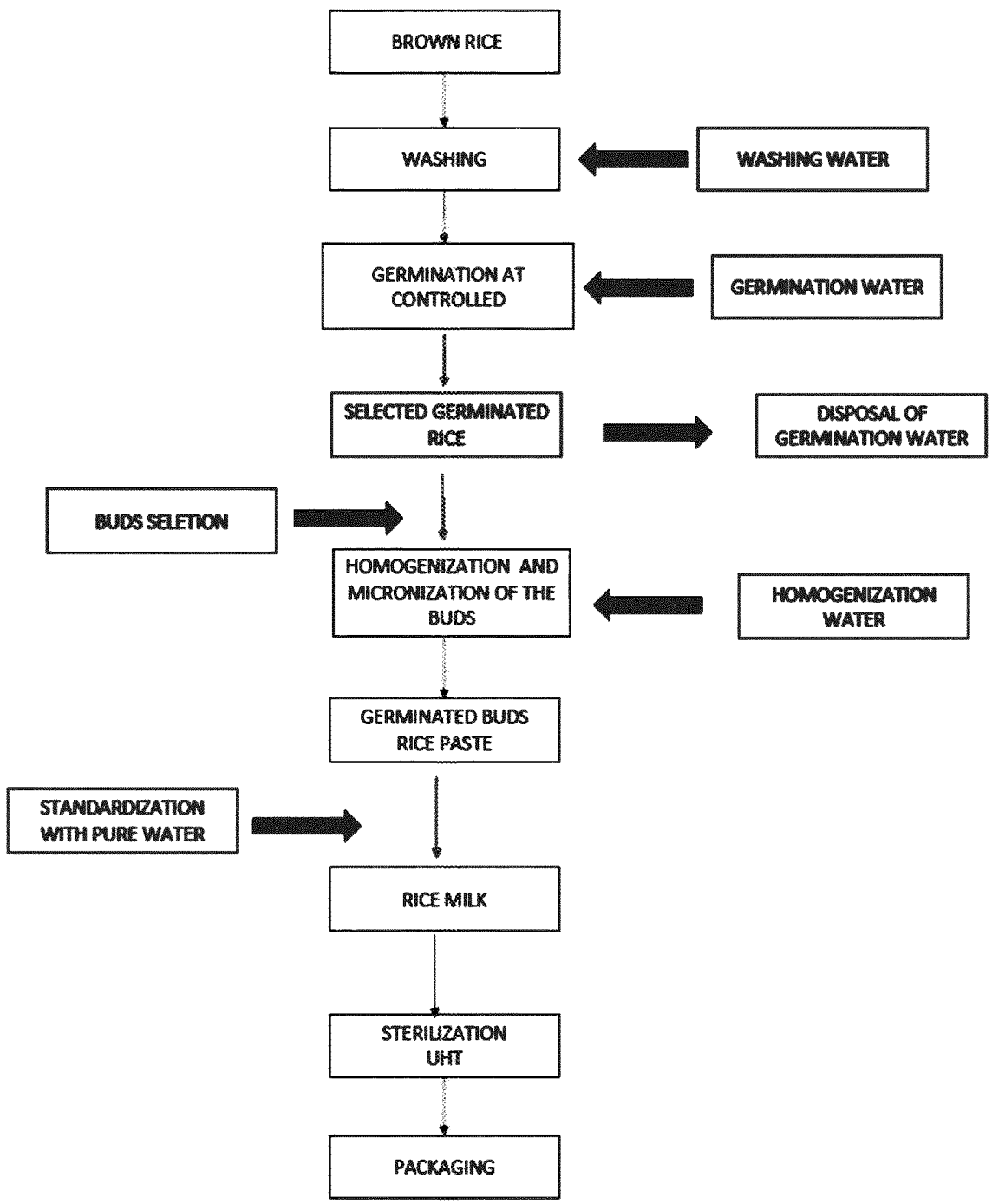

FIG. 11 is a schematic representation of the production flow chart of VGF (a germinated rice (*Oryza sativa*) water extract).

Figure 12:
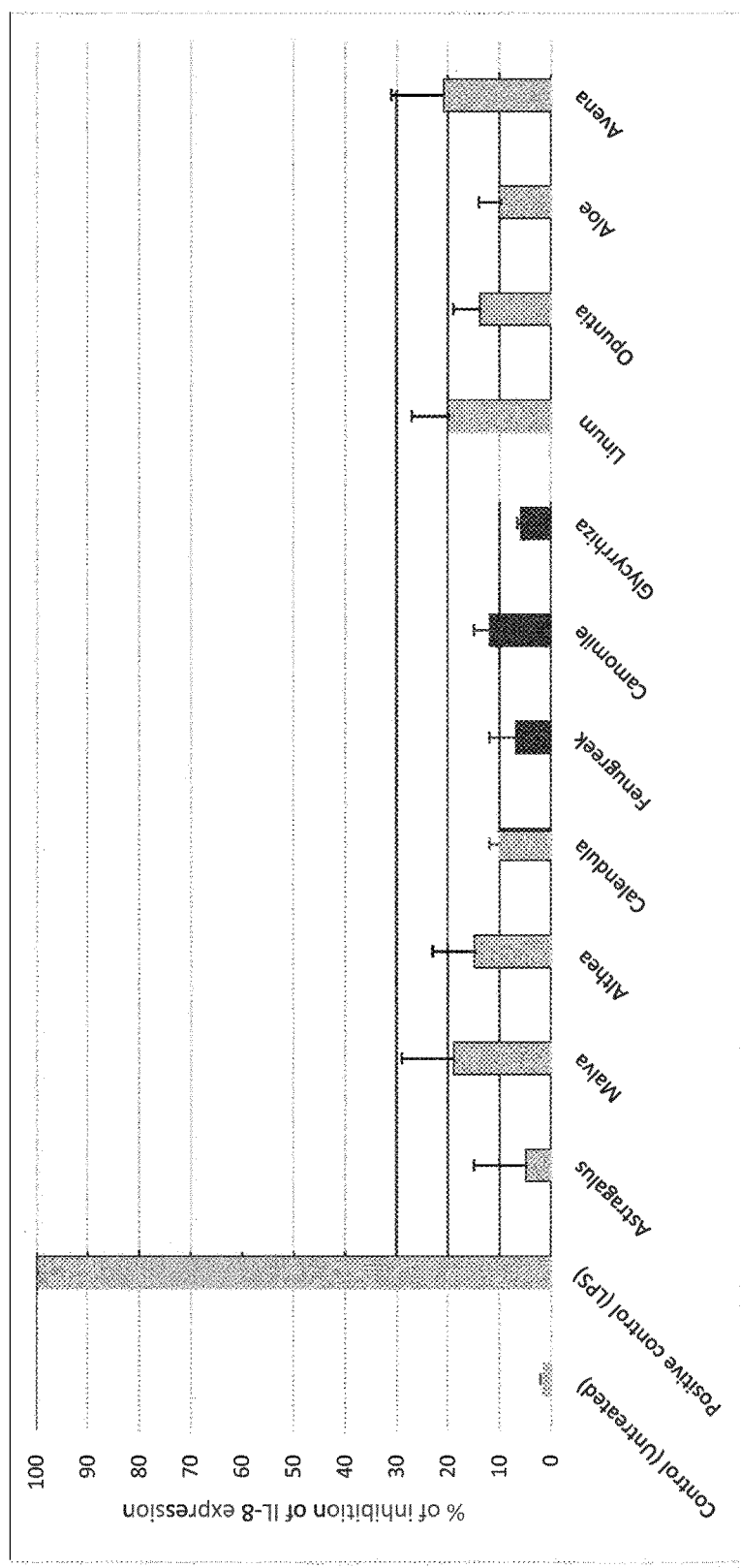

FIG. 12 shows a graphical representation of the effects of different plant extracts (as shown on X axis) on esophageal epithelial cells when evaluating the soothing activity of the composition of the invention. Stimulation with bacterial Lipopolysaccharide (LPS, 500 ng/ml) for 6 h was considered as positive control for inducing the expression of IL-8; following each plant extract was added to each cell culture in order to assess its inhibitory effect on the IL-8 expression. Total RNA was isolated and gene expression for IL-8 was evaluated by RT-qPCR (*=P<0.05 all extracts caused a significant inhibition of IL-8 compared to the positive control).

The characteristics and advantages of the composition of the invention will be clearer from the detailed description which follows of the tests and results which have led to its definition and are reported in the Examples.

DETAILED DESCRIPTION OF THE INVENTION

The present invention concerns a composition comprising a combination of a mucoadhesive component in the range from 0.05-20% by weight, an emollient component in the range from 0.02-20% by weight, hydrating and mucoprotective component i.e. sodium hyaluronate in the range from 0.01-15% by weight and epithelizing component i.e. one or more amino acids, or collagen, chondroitin, glucosamine in the range from 0.02-5% by weight for use in the treatment of epithelial lesions, wherein said emollient component, which exerts an antiinflammatory effect helping to reduce local irritation, is an extract chosen from the group consisting of *Oryza sativa, Trigonella foenum graecum, Malva sylvestris, Althea officinalis, Matricaria chamomilla, Melissa officinalis, Glycyrrhiza glabra, Calendula officinalis, Vitis vinifera, Borago officinalis, Linum usitatissimum, Opuntia ficus-indica, Prunus dulcis, Aloe barbadensis* and *Avena sativa*.

In a preferred embodiment of the present invention said emollient component is *Oryza sativa*. In a further embodiment said emollient component is *Trigonella foenum graecum*.

Surprisingly it has been found that the emollient component of the composition of the present invention may be *Oryza sativa* in combination with or replaced by one or more of: *Trigonella foenum-graecum, Malva sylvestris, Althea officinalis, Matricaria chamomilla, Melissa officinalis, Glycyrrhiza glabra, Calendula officinalis, Vitis vinifera, Borago officinalis, Linum usitatissimum, Opuntia ficus-indica, Prunus dulcis, Aloe barbadensis, Avena sativa, Hippophae rhamnoides, Acacia* spp.; *Acanthus mollis; Anacardium occidentale, Astracantha adscendens; Astracantha* spp., *Astragalus membranaceus; Astragalus verus, Calendula arvensis; Castilla elastica, Ceratonia siliqua, Cetraria islandica. Commiphora gileadensis, Corymbia citriodora/ Eucalyptus citriodora, Cucumis sativus, Cydonia oblonga, Drosera* spp., *Eucalyptus globulus, Eucalyptus smithii, Fucus vesiculosus, Grindelia* spp., *Helianthus annuus, Hordeum vulgare, Leucanthemum vulgare, Lobaria pulmonaria, Macadamia temifolia, Manihot esculenta, Ophioglossum vulgatum, Phoenix dactylifera, Platago* spp., *Prunus armeniaca, Prunus dulcis, Roccella phycopsis, Rosa centifolia, Rosa gallica, Sisymbrium officinale, Solanum tuberosum, Sorghum bicolor, Verbascum* spp., and *Ziziphus jujube*.

The use of the composition of the present invention may be applied to the veterinary field.

The sodium hyaluronate (the sodium salt of hyaluronic acid) of the invention has lubricating and hydration actions and allows the reduction of the friction and limits discomfort mainly due to dryness and irritation. Such an action is due to hyaluronic acid and its salts i.e. sodium hyaluronate. All variants resulted effective including low, medium and high molecular weight, primarily medium molecular weight. In the present invention, sodium hyaluronate contributes to restore the normal hydration of irritated tissue and sustain the barrier effect on the application site (skin and mucosa), thus preventing the tissue erosion and injuries induced by irritant stimulation. In addition, the synergic complex of sodium hyaluronate and amino acids (mainly proline, hydroxylproline, and glutamine) sustains the physiological repairing process of the injured tissue.

In a preferred embodiment, said mucoadhesive component, which has the property of allowing the adhesion of the composition to the tissue, is chosen from the group consisting of Poloxamers, Copolymers of ethylene oxide and propylene oxide, Carbomers, Poly acrylic acids, Tragacanth gum, Karaya gum, Guar gum, Xanthan gum, Acacia gum, Arabic gum, Sodium alginate, Mannuronic acid, Glucuronic acid, Soluble starch, Gelatin, Pectin, Chitosan, Lectins, Hydroxypropyl methyl cellulose, Methyl cellulose, Carboxymethycellulose, and all cellulose derivatives, Polyvinyl alcohol and Poly vinyl pyrrolidone and their derivatives or a combination thereof.

In order to be effective, the composition of the invention must adhere to the tissue, exert protective effects i.e. both soothing and hydrating and promote the wound healing by enhancing the cell proliferation.

Mucoadhesive action is due to polymers (i.e. carbomer and poloxamer) able to adhere to the tissue such as skin and mucosa. Bioadhesion (or mucoadhesion) is generally understood to define the ability of a biological or synthetic material to "stick" to a mucous membrane by interacting with mucin, resulting in adhesion of the material to the tissue for a protracted period of time. In such situations, viscous hydrogel layer protects the mucosa.

Carbomer is a high molecular weight polymer of acrylic acid crosslinked with allyl ethers of pentaerythritol. Carbomer has been used worldwide for many years to thicken, modify flow characteristics, emulsify, and suspend insoluble ingredients. Recently, interest in their mucoadhesive properties has grown dramatically. Carbomer polymers are assessed for bioadhesive drug delivery systems in many pharmaceutical applications such as mucoadhesive buccal hydrogel, gastro-intestinal applications, vaginal gels, ophthalmic products etc.

Poloxamer is a high molecular weight polymer used primarily as thickening agent, gel former, dissolution enhancer, lubricant and wetting agent as well as co-emulsifier in pharmaceutical formulations and cosmetics such as toothpastes, gargles and mouthwashes.

A peculiar feature of these polymers is their thermo-gelling property, due to their capacity to self-assemble into micelles in an aqueous solution. Temperature increase leads the rearrangements of poloxamer micelles into a complex structure forming a gel.

Poloxamer exerts muco-adhesive properties mainly in presence of other polymers. For example, its combination with carbomer enhances the gel strength and bioadhesive force; such combination leads to promising results according to higher viscosity and bioadhesiveness on the oral and sublingual mucosa.

The addition of hyaluronic acid caused a modulation in the rheological properties of the poloxamer. Mucoadhesion tests showed an increased interaction with mucin for ocular applications.

Poloxamer is a GRAS (generally recognized as safe) excipient, US FDA approved for pharmaceutical formulations and not damaging for the mucosal membranes.

In a preferred aspect, said emollient component is an extract of *Oryza sativa* and said mucoadhesive component is a combination of Poloxamers and Carbomers. In the composition of the present invention, the amino acids, or collagen, chondroitin, and glucosamine have a mucoprotective action favoring the reparative processes of damaged epithelium. Such an action is due primarily to the action of the amino acids, which contribute and support protein synthesis. These compounds are commonly found in all tissues of human body and contribute to cell proliferation and improve extra cellular matrix formation. Theoretically all amino acids (including phenylalanine, alanine, hysoleucine, leucine, lysine, methionine, threonine, tryptophan, valine, proline, hydroxyproline, glutamine, histidine, cysteine, tyrosine, glycine, arginine, taurine), both L- or D-isomers, are effective to this end. Preferred amino acids are proline, hydroxyproline and glutamine.

Mucoprotective action is due to the barrier layer formed on the tissue and mucosa, which prevents the tissue erosion and injuries induced by irritant compounds, such as gastric acids flowed back into the esophagus in case of GERD. In addition, the synergic combination of hyaluronic acid and aminoacids (mainly proline, hydroxylproline, and glutamine) sustains the physiological repairing process of the injured tissue.

Hyaluronic acid is one of the fundamental components of the extracellular matrix, able to give the tissue resistance and tonicity. Chemically, it is a glycosaminoglycan consisting of thousands of disaccharide units formed in turn by residues of glucuronic acid and N-acetylglucosamine, alternatively between β1→4 and β1→3 glycosidic bonds, while intramolecular hydrogen bonds stabilize the three-dimensional conformations. Hyaluronic acid is mainly present in the extracellular matrix where it contributes to maintain the degree of hydration, turgidity, plasticity and viscosity. In addition to its structural function, it has been undertaken in many key processes such as tissue regeneration, morphogenesis, matrix organization. A therapeutic goal has been examined for the treatment of various disorders; local administration are effective for the treatment of aphthae, ulcers and wounds thanks to the barrier effect ensuring the protection of the injured area. Its sodium salt, sodium hyaluronate, is widely used in skin care cosmetics. There is evidence of its effectiveness in promoting tissue regeneration. In fact, it is used against inflammation and ulcerative lesions of the mouth (aphthae, stomatitis, etc.), in particular those resulting from chemo and radiotherapy, rapidly reducing pain and promoting healing (Nolan et al. 2006). In addition, it promotes the processes of re-epithelialization of the irritated and damaged mucosa and promotes the healing of ulcers and microlesions. A formulation based on hyaluronic acid has been tested in an ex vivo study in which the porcine esophageal mucosa was exposed to an acid solution (HCl) to induce a tissue damage and then treated with the formulation containing hyaluronic acid. Glutamine has multiple effects on the structure and function of human body; it is an amino acid able to sustain the physiological proliferation process of our cells, such as intestinal epithelial cells (IEC).

Proline. An in vitro study demonstrated that the proline-loaded hydrogels increased cell viability ($p<0.01$), migration, proliferation and wound healing activity ($p<0.001$) compared to chitosan hydrogels. The same study also showed that the viability of NIH 3T3 L1 cells was not affected by the treatment with proline loaded hydrogels.

Hydroxyproline is a non-essential amino acid found in collagen and few other extracellular animal proteins. It plays a crucial role in collagen synthesis and stability of the triple-helical conformation of collagen and associated tissues. Various abnormalities in hydroxyproline metabolism have been shown to play key roles in the pathophysiology and pathogenesis of different diseases, for example, its decreased level is a marker of poor wound-healing tissue capability.

The composition of the invention is suitable for use in the treatment of epithelial lesions, wherein said epithelial lesions affect the oral and/or gastrointestinal tract, the rectum, the vagina or the skin.

In a preferred aspect, said epithelial lesions affect the oral and/or gastrointestinal tract, and are characterized by impaired tissue following gastro-esophageal reflux or gastric ulcers, esophagitis, infections (bacterial, viral and fungal ones), lesions from drugs abuse (i.e. NSAIDs), chemotherapy and radiotherapy, allergy, corrosive substances etc.

More preferably said epithelial lesions are symptoms of in the manifestation of gastro-esophageal reflux disease.

The composition of the invention may be used for the treatment of skin lesions such as skin ulcers, skin injuries including those derived from atopic dermatitis, burns, wounds, acne or insect bites.

The composition of the invention may be for topical application or for oral administration.

The composition of the invention may be administered by oral administration, and in such a case the composition is in the solid form of a tablet, capsule, powder, granules, toothpaste, oral cream or gel, candy, dissolvable pill or strip, chewing gum, lozenge or powder or in liquid form of suspension, emulsion, solution, oral spray or mouthwash.

In a preferred aspect, the liquid formulation is for oral administration, and is packed in a stick for single use or in a bottle.

According to some embodiments, the composition of the invention, for use in the treatment of epithelial lesions comprises:
  carbomer (poly acrylic acid) in the range from 0.05% to 5%;
  sodium hyaluronate in the range from 0.01% to 15%;
  poloxamer (copolymers of ethylene oxide and propylene oxide) in the range from 0.1% to 15%;
  *Oryza sativa* extract in the range from 0.2% to 20%; and
  one or more amino acids in the range from 0.025% to 5%, wherein said percentages are by weight of the total weight of the product (w/w).

In a further embodiment the *Oryza sativa* extract is replaced by a *Trigonella foenum graecum* extract in the range from 0.2% to 20%, preferably 2%.

The remaining may be water, sweetener, flavouring and preservatives.

According to some further embodiments, the composition of the invention comprises:

0.5% carbomer (poly acrylic acid);

0.15% sodium hyaluronate;

1% poloxamer (copolymers of ethylene oxide and propylene oxide);

2% *Oryza sativa* extract;

0.25% proline, 0.25% glutamine and 0.25% hydroxyproline, wherein said percentages are by weight of the total weight of the final product (w/w).

In a preferred aspect, said composition is in a liquid form for oral use.

In a second aspect thereof, this invention moreover provides a composition comprising:

carbomer (poly acrylic acid) in the range from 0.05% to 5%;

sodium hyaluronate in the range from 0.01% to 15%;

poloxamer (copolymers of ethylene oxide and propylene oxide) in the range from 0.1% to 15%;

*Oryza sativa* extract in the range from 0.2% to 20%; and one or more amino acids in the range from 0.025% to 5%, wherein said percentages are by weight of the total weight of the product (w/w).

In a preferred aspect, said composition comprises:

0.5% carbomer (poly acrylic acid);

0.15% sodium hyaluronate;

1% poloxamer (copolymers of ethylene oxide and propylene oxide);

2% *Oryza sativa* extract;

0.25% proline, 0.25% glutamine and 0.25% hydroxyproline, wherein said percentages are by weight of the total weight (w/w).

In a further embodiment the *Oryza sativa* extract is replaced by a *Trigonella foenum graecum* extract in the range from 0.2% to 20%, preferably 2%. Under a still further aspect the present invention describes a method of treating a subject in need thereof, said method having the step of administering a composition herein described.

EXAMPLES

Reference is now made to the following examples, which together with the above descriptions illustrate some embodiments of the invention.

Example 1

Preparation of the Composition

Composition for Use in Gastro-Esophageal Reflux

The invention is a liquid formulation for oral administration, packed in stick for single use or bottle, indicated for the treatment of gastroesophageal reflux symptoms. It exerts a protective action promoting the repairing processes of the esophageal mucosa, which can be injured by the gastric content flowed back into the esophagus.

TABLE 1

Example of COMPOSITION of the invention

| Ingredient list | Quantity/dose (10 ml) | % |
| --- | --- | --- |
| CARBOMER | 50 mg | 0.5% |
| SODIUM HYALURONATE | 15 mg | 0.15% |
| PROLINE | 25 mg | 0.25% |
| GLUTAMMINE | 25 mg | 0.25% |
| HYDROXYPROLINE | 25 mg | 0.25% |
| POLOXAMER 407 | 100 mg | 1% |
| VGF ™ (*Oryza sativa*) | 200 mg | 2% |

TABLE 2

Example of COMPONENTS RANGE

| Ingredient list | FROM | TO |
| --- | --- | --- |
| CARBOMER | 0.05% | 5% |
| SODIUM HYALURONATE MMW | 0.010% | 15% |
| PROLINE | 0.025% | 5% |
| GLUTAMMINE | 0.025% | 5% |
| HYDROXYPROLINE | 0.025% | 5% |
| POLOXAMER 407 | 0.1% | 15% |
| VGF ™ (*Oryza sativa*) | 0.2% | 20% |

VGF ™ is a germinated rice (*Oryza sativa*) water extract.

Composition for Use in Oral Mucosa Ulcers and Lesions

The invention is a gel contained in a tube (different volume) indicated for the treatment of buccal ulcers. It exerts a protective action due to its mucoadhesive properties, which make the product able to adhere to the oral mucosa and promote the repairing processes of the oral mucosa, which can be injured for several issues including mucositis, stomatitis, drugs therapies, bacterial and viral infections etc.

Composition for Use in Skin Ulcers

The composition according to the invention is in the form of a gauze or a patch (different dimensions), filled with a solution containing the ingredients listed above, indicated for the treatment of skin ulcers. It exerts a protective action due to its mucoadhesive properties which make the product able to adhere to the injured skin and promote the repairing processes in the tissue, which can be injured for several reasons including diabetes, decubitus sores, etc.

Composition for Use in Skin Injuries Including Those Derived from Atopic Dermatitis, Psoriasis, Burns, Wounds, Sunburns.

The skin barrier plays a crucial role in the pathophysiology of dermatitis. It is pivotal for preventing the penetration of pathogens in damaged skin and subsequent infection and protecting also from excessive water loss. Compounds exerting both skin barrier effects and soothing activity are potentially able to restore the skin physiological functions. In particular, barrier effect is needed in order to lower skin damage.

The composition according to the invention is in the form of a gel or cream for local (topic) administration, containing the ingredients listed above, indicated for the treatment of skin lesions, wound and burns. It exerts a protective action due to its mucoadhesive properties which make the product able to adhere to the injured skin and promote the repairing processes in the tissue.

Composition for Use in Skin Injuries Including Burns, Wounds, Sunburns.

The composition according to the invention is in the form of a spray (contained in a bottle with or without propellant, of different volume) for local (topic) administration, containing the ingredients listed above, indicated for the treatment of skin lesions, wound, burns and sunburns. It exerts a protective action due to its mucoadhesive properties which make the product able to adhere to the injured skin and promote the repairing processes in the tissue.

Example 2

Experimental Models of Esophageal Mucosa Damage

The adhesive, barrier, soothing and repairing effects of a composition of the invention was studied in different experimental models of esophageal epithelial cells (i.e. CP-A and COLO-680N) by simulating in vitro the damage induced by gastric content on the esophagus.

The composition (or formulation) that was tested has the following composition:

| | |
|---|---|
| CARBOMER | 0.5% |
| SODIUM HYALURONATE | 0.15% |
| PROLINE | 0.25% |
| GLUTAMMINE | 0.25% |
| HYDROXYPROLINE | 0.25% |
| POLOXAMER 407 | 1% |
| VGF ™ (Oryza sativa) | 2% |

All percentages are calculated on the final weight of the product and the remaining is water, sweetener, flavouring and preservatives.

The composition may be formulated also by varying the percentages of the components or by modifying the components within the definition of claim 1.

To this aim, we incubated the cell monolayer with a medium (named BSC) containing bile salts cocktail, pepsin and pH 2.5 (thus simulating the gastric juice). We proved that our formulation exerted all the investigated protective actions on the irritated tissues. Interestingly and surprisingly, we found that the combination of components exerted a significant repairing effects in both cell lines. Such results are very surprising because when the compounds were tested alone, we did not find any significant repairing effect while only the combination was able to do it.

Figure 1:
FIG. 1 shows a photo of a confluent monolayer of COLO-680N esophagus cells cultured in a 24 well plate, scraped with a pipette tip. After the induction of the scratch at the middle of monolayer (dashed line), untreated COLO-680N cells (negative control) migrate from the margin of wound (continuous line) towards the center and completely close the wound within 24 hours.
Figure 3:
FIG. 3 shows a photo of a confluent monolayer of COLO-680N esophagus cells treated with BSC and then incubated with placebo and cultured in a 24 well plate. Also in this case, the COLO-680N cells are not able to close the wound within 24 hours and do not migrate from the margin of wound (continuous line).
Figure 4:
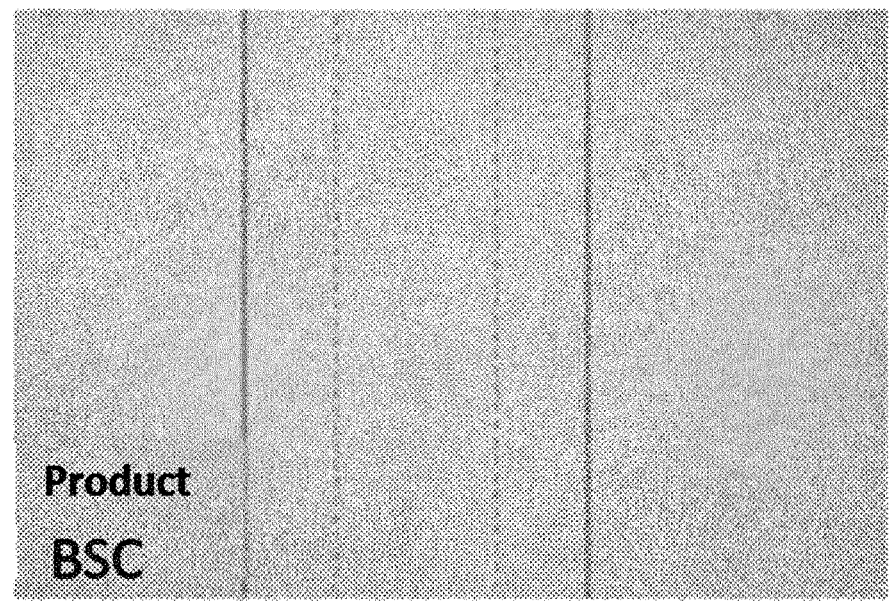
FIG. 4 shows a photo of a confluent monolayer of COLO-680N esophagus cells treated with BSC and then incubated with the composition of the invention. The repairing effect of the composition can be seen since, after the induction of the wound in the monolayer center, the cells migrate from the margin of the scratch (continuous line) towards the middle, reducing significantly (P<0.05) the wound within 24 hours.
Figure 5:
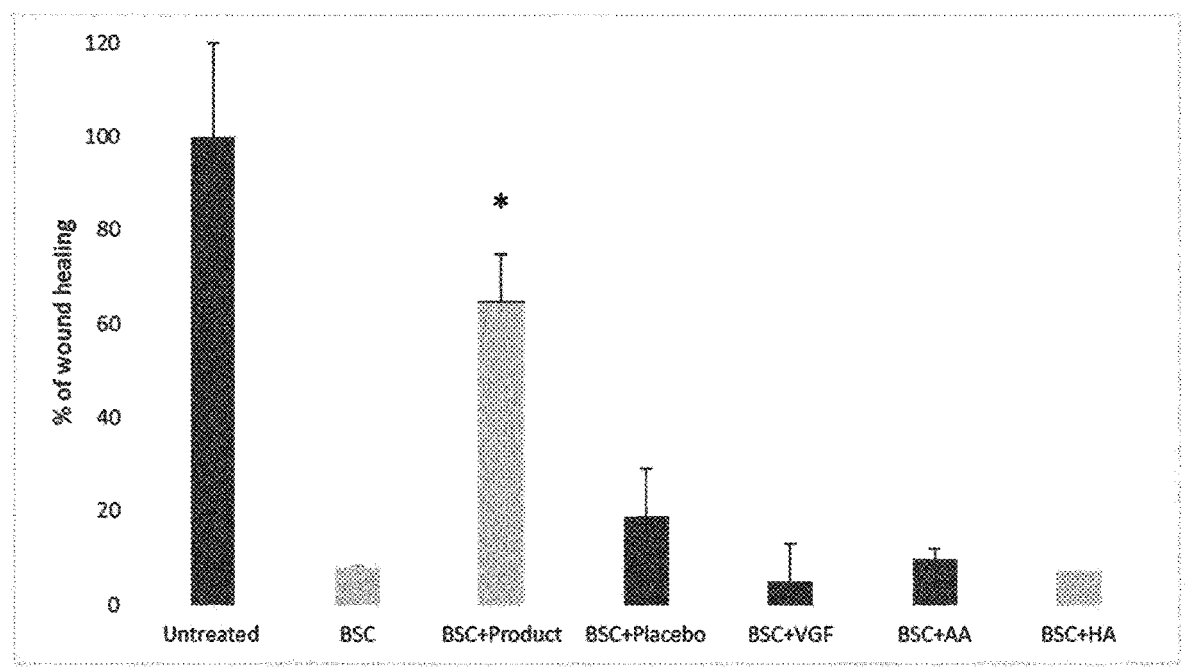
FIG. 5 is a graph which shows the results of a quantification of the data by assessing the number of cells, their movements, and the distance covered by each cell during the observation period. The * means that the difference between the cells treated with the composition of the invention and those treated with placebo is statistically significant (P<0.05) showing that our product exerts a wound healing effect that the placebo (the mucoadhesive component) does not exert. The figure also shows that the components of the invention do not exert wound healing effect when tested alone (VGF™ is the rice extract, HA is sodium hyaluronate and AA corresponds to amino acids).

The significant repairing effect was assessed as described in FIG. 1-5. Confluent monolayers of COLO-680N esophagus cells, cultured in a 24 well plate, were scraped with a pipette tip and, after washing twice with PBS, were incubated with BSC (irritant medium simulating the gastrointestinal juice) or culture medium alone as a negative control. After 2 h of incubation under standard culture condition (at 37°, 5% $CO_2$), our formulation was added for 3 h at 37° C., 5% $CO_2$. Wound closure (healing) was evaluated up to 24 h under a Leica DMIL inverted microscope (Leica Microsystem) and images were collected using a Canon Powershot A640 digital camera (Canon). The cellular movements, distance and cell number were used for quantitative evaluations. The images were analyzed by ImaJ software. Results were analyzed by statistical method for assessing the significance compared to both controls and single component of the invention; the differences were considered significant for p<0.05 (FIG. 5). FIG. 1 shows that after the induction of the scratch at the middle of monolayer (dashed line), untreated COLO-680N cells (negative control) migrate from the margin of wound (continuous line) towards the center and completely close the wound within 24 hours.

Figure 2:
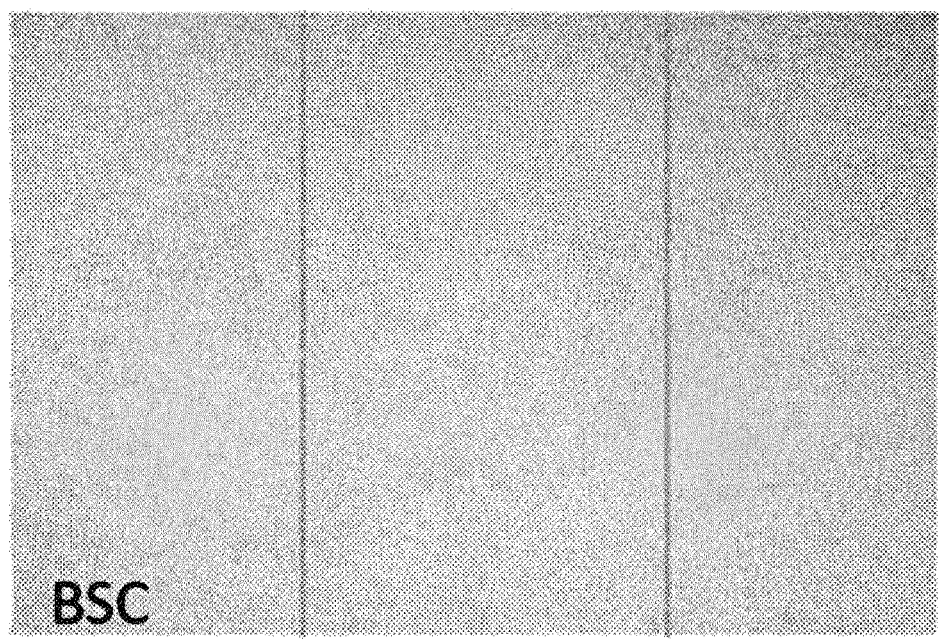
FIG. 2 shows a photo of a confluent monolayer of COLO-680N esophagus cells treated with BSC cultured in a 24 well plate (BSC is an irritant medium simulating the stomach content containing bile salts, pepsin acidic pH). On the contrary to the untreated cells, COLO-680N cells treated with the BSC medium (positive control) are not able to close the wound within 24 hours; in fact, they do not migrate from the margin of wound (continuous line).

On the contrary, as shown in FIG. 2, COLO-680N cells treated with BSC (positive control) are not able to close the wound within 24 hours; in fact, they do not migrate from the margin of wound (continuous line).

We obtained similar results from COLO-680N cells treated with BSC and then incubated with placebo (FIG. 3).

Unexpected results were obtained when we treated COLO-680N cells with BSC and then incubated with our formulation (FIG. 4). Our findings clearly highlight the repairing effect of our formulation due to its synergic composition. In fact, after the induction of the wound in the monolayer center, the cells migrate from the margin of the scratch (continuous line of FIG. 4) towards the middle, reducing significantly the wound within 24 hours.

We quantified these qualitative data by assessing the number of cells, their movements, and the distance covered by each cells during the observation period, and the results are shown the graph of FIG. 5. The * means that the difference between the cells treated with our formulation and those treated with placebo is statistically significant (P<0.05) showing that our product exerts a wound healing effect that the placebo does not exert.

The results indicated in the graph of FIG. 5 show the quantitative wound healing effect of the composition of the invention compared to negative control (untreated), positive control (BSC), placebo (product without the functional active components) and individual components of the invention tested alone.

The results clearly show that untreated cells are able to completely close the scratch experimentally induced in the monolayer with a pipet tip, thus confirming the usability of this cellular model for the outcome we wanted to assess (i.e. repairing effect). On the contrary, cells treated only with BSC were not able to close the wound. Surprisingly, the composition of the invention was able to significantly revert the negative effect of BSC and promote the wound healing, as shown by the reduction of the scratch. Such an effect was not exerted by neither the placebo nor single components meaning that the specific mixture of functional active components present only in the composition of the invention can be useful to promote the tissue healing in an esophageal mucosal model of reflux damage.

Example 3

Experimental Cell Model of the Soothing and Repairing Effects

The following experiments demonstrate the anti-irritating and soothing effects of the composition of the invention, in our esophageal cell models in vitro. Such effects are very important for the therapeutic effectiveness of the described composition, because they show that the product is also able to reduce the mucosal irritation caused gastric content and, as a consequence, contribute to promote the repairing effects.

Figure 6:
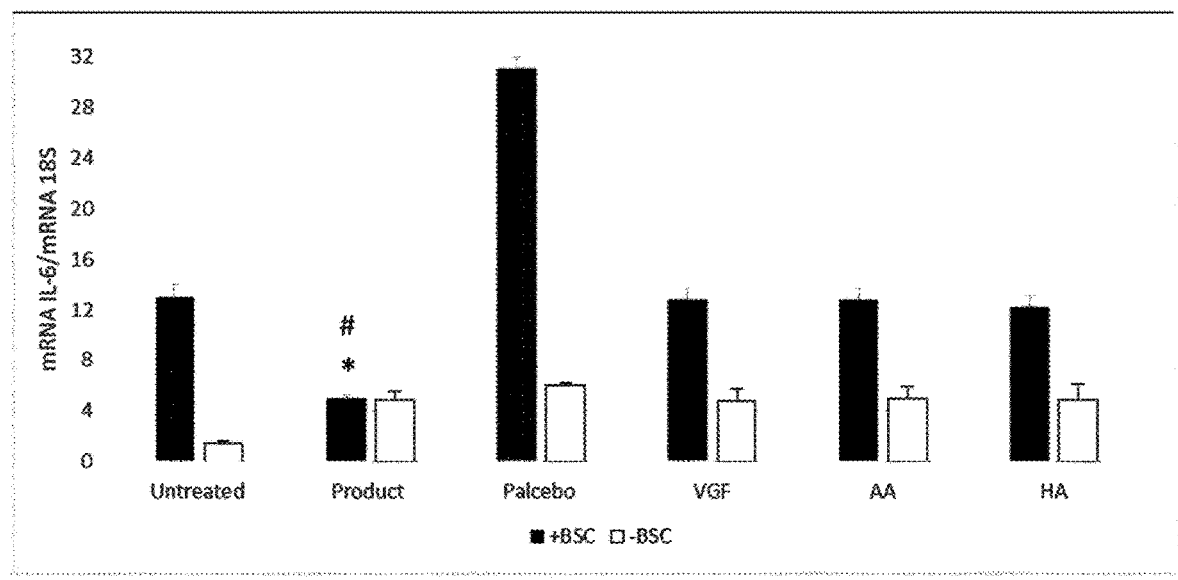
FIG. 6 is a graph of the results obtained when evaluating the anti-irritative properties of the composition of the invention when evaluated by RT-qPCR (Real Time-quantitative Polymerase Chain Reaction). The effect of our invention on irritation was assessed by measuring the expression of interleukin (IL)-6, which is a proinflammatory cytokine, by human esophagus cells. A confluent monolayer of human esophagus cells (COLO-680N esophageal cells were used) were incubated with the invention, placebo or each component of the invention alone (i.e. rice extract, amino acids and sodium hyaluronate) for 1 hour at 37° C., 5% $CO_2$; treated and not treated cells have been incubated with BSC medium for 4 hours and IL-6 expression evaluated by RT-qPCR. The * and ** mean that the difference between the cells treated with the composition of the invention and those treated with placebo is statistically significant (*P<0.05; #P<0.01) showing that our product exerts an anti-irritative and anti-inflammaotry effect that neither the placebo (mucoadhesive component alone) nor the components of the invention tested alone exert (VGF™ is the rice extract, HA is sodium hyaluronate and AA corresponds to amino acids).

In order to evaluate the anti-irritative properties of the composition, human esophagus cells were seeded in a 24 well/plate and incubated with the product or placebo (1:4) for 1 h at 37° C., 5% $CO_2$ (standard experimental conditions). Then, treated and not treated cells were incubated with BSC for 4 h for simulating the tissue irritation happening during reflux. Total RNA was isolated and gene expression for pro-inflammatory cytokine IL-6 was evaluated by RT-qPCR. The results are shown in the graph of FIG. 6.

Figure 7:
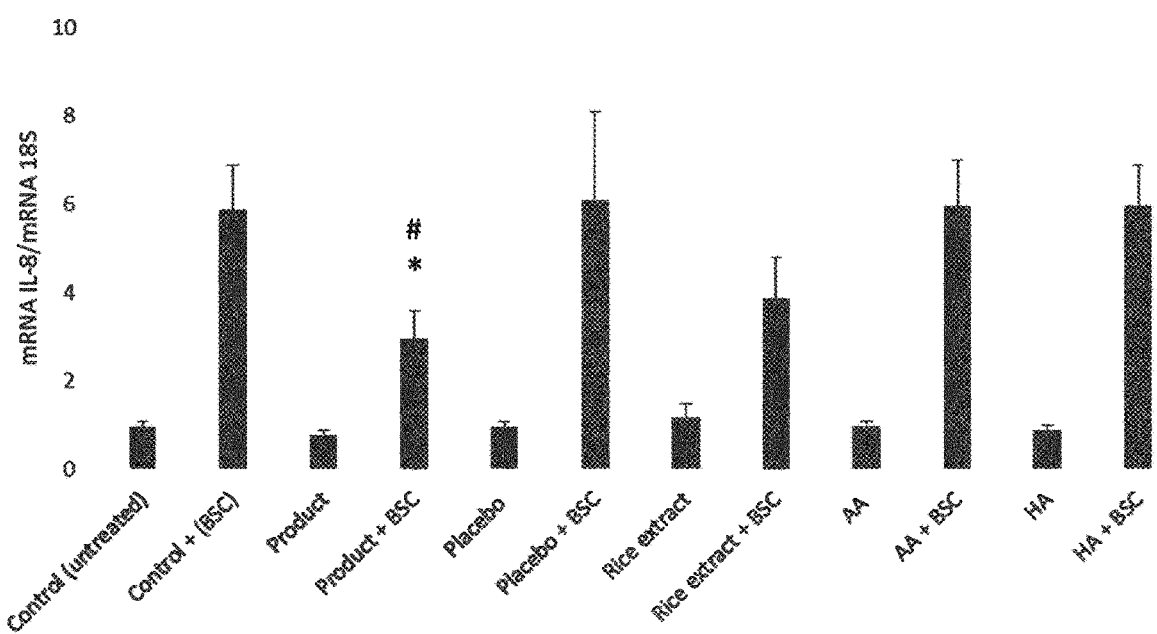
FIG. 7 is a graph of the results obtained when evaluating the soothing activity of the composition of the invention. 24 well/plates with confluent esophageal cells were incubated with BSC medium for 1 h and subsequently treated with our product, placebo (1:4) or any component of the invention (rice extract, amino acids or sodium hyluronate) for 4 h. Total RNA was isolated and gene expression for chemokine IL-8 was evaluated by RT-qPCR (*=P<0.05). The figure shows that the composition of the present invention exerts an anti-irritative and anti-inflammatory effect that neither the placebo nor the components of the invention tested alone exert.

In order to evaluate if the soothing activity of our product, 24 well/plates with confluent esophageal cells were incubated with BSC for 1 h and subsequently treated with our product, placebo (1:4) or each component of the invention for 4 h. Total RNA was isolated and gene expression for chemokine IL-8 was evaluated by RT-qPCR. The results of the evaluation experiments are shown in FIG. 7.

These results clearly show that our product exerts a soothing and anti-irritative action on the irritation induced by BSC on esophageal cells. The effect of rice extract has been shown for the first time and contribute to the efficacy of our product.

Example 4

The Soothing Effects of Plant Extracts

The following experiments demonstrate the anti-irritating and soothing effects of plant extracts which can be used to prepare the composition of the invention, in our esophageal cell models in vitro. Such effects are very important for the therapeutic effectiveness of the described composition, because they show the possible soothing and anti-inflammatory effect of the emollient component of the invention.

In order to evaluate each emollient component, human esophagus cells were seeded in a 96 well/plate and incubated with the bacterial Lipopolysaccharide (LPS, 500 ng/ml) for 6 h for inducing the expression of IL-8. Such treatment was considered as a positive control.

After LPS stimulation, cells were treated with each of the plant extract listed below: *Astragalus membranaceus, Malva sylvestris, Althea officinalis, Calendula officinalis, Trigonella foenum-graecum* (Fenugreek), *Matricaria chamomilla, Glycyrrhiza glabra, Linum usitatissimum, Opuntia ficus-indica, Aloe barbadensis, Avena sativa*.

Total RNA was isolated and gene expression for pro-inflammatory cytokine IL-8 was evaluated by RT-qPCR. The results are shown in the graph of FIG. 12.

These results clearly show that each selected plant extract exerts a soothing and anti-inflammatory action on esophageal cells (p<0.05 vs LPS) since all extracts exert a significant (P<0.05) inhibition of IL-8 expression after LPS stimulation in vitro using epithelial esophageal cells.

Example 5

Clinical Study

Giellepi S.p.A. carried out a clinical investigation on the product described by the present invention, wherein the emollient component is an *Oryza sativa* extract, aimed to assess its clinical efficacy the GERD symptoms relief in comparison to the placebo.

The clinical trial was performed in collaboration with an international CRO named BioAgile Therapeutics Pvt. Ltd., Bangalore (India). The study was conducted in accordance with international laws and guidelines about clinical investigation in humans such us the Good Clinical Practice guidelines as issued by the International Conference on Harmonization (ICH/135/95, July 2002) guidelines, the Declaration of Helsinki (64th WMA General Assembly, Fortaleza, Brazil, October 2013) and ISO 14155.

The study design was a randomized (1:1), double-blind, parallel-group, placebo controlled, interventional study in patients with gastroesophageal reflux disease. The clinical trial was conducted according to the protocol (BAG-01-2018 Version No: 1.0, Dated: Apr. 28, 2018) as monocentric study at the Rajalakshmi Hospital, No. 21/1, Lakshmi pura main road (opp. Lakshmipura lake), Vidhyaranyapura post, Bangalore-560097 and it started only after receiving the approval by the institutional ethical committee (RH/IEC/AP-010/2018 of Jun. 5, 2018).

The primary endpoint was to assess the efficacy in terms of proportion of patients with a significant remission of Gastroesophageal reflux disease (GERD) symptoms.

The secondary endpoints were to evaluate:
The safety and tolerability of Investigational Product;
Number of patients with 50% reduction of symptoms at the end of treatment;
Number of days required to first achieve 24 hours without heartburn;
Days to achieve first daytime or night time heartburn-free interval;
Heartburn Severity Index; and
Quality of life.

40 patients with gastro-esophageal reflux were recruited, after signing the informed consent, and randomized into 2 groups (20 patients each) treated with either our formulation (verum) or placebo for 14 days.

A series of screening evaluations were performed after taking informed consent, in order to determine whether participants meet the selection criteria for the trial. Screening evaluations included general physical examination by the medical doctor, demographics (including gender, date of birth, age, height, weight, smoking and drinking habits), vital signs (blood pressure, oral temperature and pulse rate), medical history and concomitant medications. Subjects undergone endoscopy (if not done in last 3 months) for diagnostic reason and blood sample collection for lab investigations (haematology, biochemistry, serology), ECG and urine pregnancy test. Finally, the rapid antigen stool test was performed in order to exclude *Helicobacter pylori* infection.

Inclusion criteria were:
Patients diagnosed with uncomplicated non-erosive GERD;
Patients from both sex;
Patients above 18 years old;
Patients able to provide written informed consent;
Patients who should be able to follow controlled diet (coffee and tea limited to not more than 2 cups per day; Chocolate, alcoholic beverages and spices should be reduced as much as possible).

Exclusion criteria were:
Patient with severe or erosive GERD;
Patients diagnosed with *Helicobacter pylori* infection;
Patients with any significant intestinal pathologies (for example gastric and/or duodenal ulcer, infections or inflammatory conditions of the small or large intestine, and obstructions);
Patients who underwent gastro-intestinal surgery;
Patients with malabsorption, prior gastric surgery, Barrett esophagus, esophageal stricture, pyloric stenosis, or a history of erosive esophagitis or GERD refractory to 2 months of therapy with either an H2-receptor antagonist (H2RA) or PPI;
Patients with other medical conditions different from non-erosive GERD (for example diabetes, metabolic disease, HIV positive, etc) which in opinion of the Investigator may interfere with study procedure and endpoints;
Patients with known allergy to any components of both investigational products (verum and placebo);
Patients with clinically relevant abnormal laboratory results at assessment;

Pregnant, lactating women as well as women with positive pregnancy results;

Patients with a history of alcohol or drug abuse within the past 5 years;

Currently participating or having participated in another clinical trial during the last 3 months prior to the beginning of this study.

General Procedures

Initially, eligible patients were entered into a 1-week run-in period, during which they maintained a daily diary of non-erosive GERD symptoms where they recorded the name and doses of administered medications and daily severity of symptoms. For being recruited, patients who had experienced at least 3 episodes of heartburn of moderate severity during the 7 days of run-in period.

Enrolled patients (n. 40) were randomly assigned to one treatment group (verum or placebo) according to a computer-generated sequence. Investigational products (verum or placebo) were dispensed and patients took investigational products 3 times per day (shortly after the main meals and before sleep) for 2 weeks.

Severity of daytime and nighttime heartburn and other related symptoms were recorded by each patient daily, for the 2-weeks treatment period in the patient dairy.

Proportion of patients with a significant remission of symptoms were evaluated by using Reflux Disease Questionnaire (RDQ) with Likert Scale and VAS Scale for Pain. Symptoms (heartburn, acid regurgitation, retrosternal pain and acid taste in the mouth) were rated by patients on a 5-point Likert scale (0=no symptom, 1=slight symptoms, 2=moderate symptoms, 3=severe symptoms, and 4=very severe symptoms). Pain was assessed by Visual Analogue Scale (VAS) which is a 10 cm point scale (0 corresponds to no pain and 10 is the worst pain ever felt). The primary endpoint was the treatment efficacy analysis, which was calculated as the proportion of patients with at least 3-point reduction of the total symptom score (TSS). This was calculated by collecting and computing the intensity/severity of each symptom (on the basis of the RDQ questionnaire at the final visit) and comparing it with the baseline values, obtained at the end of the run-in period. Summary statistics and ANCOVA/ANOVA for primary parameters was performed for the primary variables using baseline as covariates. Also, Student's paired t test was performed comparing baseline values with post-treatment values for both test product and placebo.

Health related quality of life (HRQL) was also assessed using the SF-36 questionnaire. Questionnaires were administered by the medical doctor. In addition to comparison with placebo, pre-treatment (baseline) and post-treatment (end of therapy) results for each group was also compared.

Patients were told to refrain from using antacid medication unless symptoms were severe enough to be intolerable, and the number of drugs consumed daily were recorded. A rescue medication (antacids) was also dispensed to all participants who could take it, if needed.

Both patients and physicians were blinded.

Finally, the compliance was assessed as the percentage of the test products used, obtained by counting the returned products at the end of the study. A treatment compliance 80% were considered acceptable and was considered for further evaluation.

Safety Assessment

Adverse event (AE) was considered as any untoward medical occurrence in a subject administered the study product (composition of the invention) which does not necessarily have to have a causal relationship with the study treatment. An AE can therefore be any unfavorable and unintended sign, symptom, or disease temporally associated with the use of the study product, whether or not considered related to the study product. Each subject was carefully monitored for the development of any adverse events. This information was obtained in the form of non-leading questions (e.g., "How are you feeling?") and from signs and symptoms detected during each examination, observations of the study personnel or spontaneous reports from the subjects.

Adverse drug reaction (ADR) was considered as all noxious and unintended responses to the study product related to any dose, meaning that a causal relationship between the test study product and the reaction is at least a reasonable possibility, i.e. the relationship cannot be ruled out. Subjects were monitored for safety during the study by analyzing the AEs. Any AEs, occurred during the course of the study, was recorded on the subject's CRF (case report form). Any subject experienced a significant adverse event was examined by a physician at the earliest possible after the event was noted, and was kept under close observation as long as medically indicated. Each AE was evaluated for duration, intensity, and relationship to (or association with) the study treatment. Additionally, the actions taken (e.g., discontinuation of study product, administration of treatment) and the resulting outcome of the AE were indicated on the CRF and notified to the ethical committee.

Figure 8:
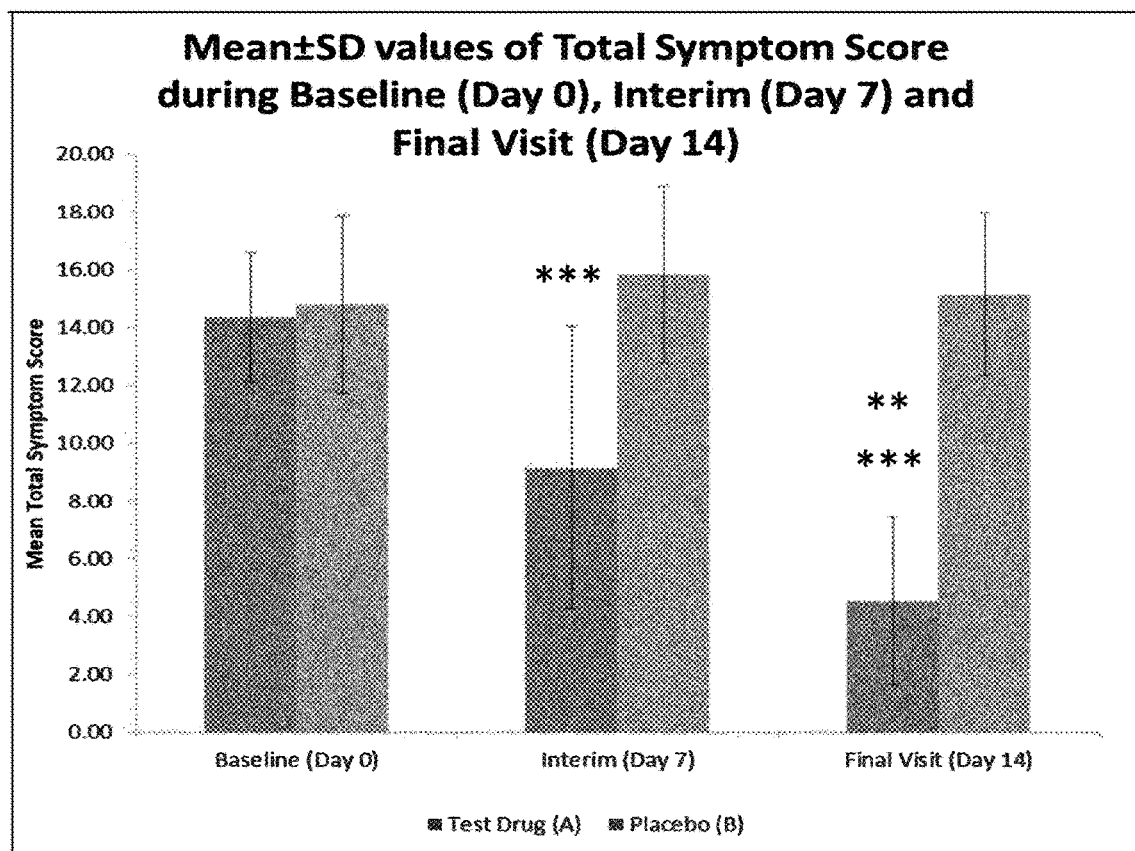
FIG. 8 shows the graph of the Total Symptom Score mean values during Baseline (Day 0), Interim (Day 7) and Final visit (Day 14) of patients treated with the composition of the invention. *P<0.0001 for Invention vs placebo; P<0.01 for Invention at Day 14 (end of treatment) vs Day 7 (interim). Dark grey: invention; Light grey: placebo.

Results 55 subjects were screened, of which 15 were excluded because they did not meet the inclusion criteria. 40 subjects were enrolled, and all completed the study. Total Symptom Score (TSS) was found to be decreased (68.3%) in subjects treated with the formulation described in the current invention. On the other hand, TSS was found to be increased (2.4%) in subjects treated with placebo (FIG. 8).

The proportion of patients treated with the formulation of the invention with at least 3-point TSS reduction was 19 patients (95%). The proportion of patients treated with placebo with at least 3-point TSS reduction was 4 patients (20%). Regarding the secondary endpoints, 18 out of 20 subjects treated with our formulation showed more than 50% TSS reduction; on the other hand, nobody for the placebo group showed 50% TSS reduction.

Based on the obtained data, after 9 days of treatment with the formulation of the invention about 50% of subjects showed 24 hours heartburn-free interval; on the contrary patients treated with placebo showed no improvement in heartburn symptoms & severity.

The heartburn severity index was calculated from results of each group after both 7 and 14 days of therapy. It decreased significantly at the end of treatment with the formulation of the invention compared to the placebo group (FIG. 9). On the other hand, no reduction in heartburn severity index found with placebo at day 14.

Quality of Life

Based on the assessment of quality of life using SF-36 questionnaire at the end of the study, patients treated with the formulation of the invention reported a significant improvement of the following parameters compared to the placebo group: Physical activity, Physical pain, General health, Vitality and Emotions. Overall, our formulation seems to be effective in improving the patient's health and wellbeing when compared to placebo (FIG. 10).

Safety Results

No adverse event occurred during the entire duration of the study. None of the treatment groups had any significant health related problems and no concomitant medications were provided. No abnormal finding was reported during physical examination during all the visits. In addition, vital signs including pulse rate, systolic blood pressure and diastolic blood pressure were in physiological ranges. FIG. 11 shows the flow chart of the production of VGF® (rice extract).

From the above description and the above-noted examples, the advantage attained by the product described and obtained according to the present invention are apparent.

The invention claimed is:

1. A method of treating epithelial lesions in subjects in need thereof, said method comprising
administering to said subjects a composition comprising:
0.5% carbomer (poly acrylic acid);
0.15% sodium hyaluronate;
1% poloxamer (copolymers of ethylene oxide and propylene oxide);
2% *Oryza sativa* extract;
0.25% proline,
0.25% glutamine and
0.25% hydroxyproline, wherein said percentages are by weight of the total weight (w/w).

2. The method according to claim 1, wherein said epithelial lesions affect the oral and/or gastrointestinal tract, the rectum, the vagina or the skin.

3. The method according to claim 1, wherein said epithelial lesions affect the oral and/or gastrointestinal tract and are characterized by impaired tissue following gastro-esophageal reflux or gastric ulcers.

4. The method according to claim 1, wherein said epithelial lesions are symptoms of in the manifestation of gastroesophageal reflux disease.

5. The method according to claim 1, wherein said epithelial lesions are skin lesions selected from the group consisting of skin ulcers, skin injuries including those derived from atopic dermatitis, burns, wounds, acne or insect bites.

6. The method according to claim 1, for topical application or for oral administration.

7. The method according to claim 6, wherein when said administration is oral administration, said composition is in the solid form of a tablet, capsule, powder, granules, toothpaste, oral cream or gel, candy, dissolvable pill or strip, chewing gum, lozenge or powder or in liquid form of suspension, emulsion, solution, oral spray or mouth wash.

8. The method according to claim 1, wherein said composition is in a liquid form for oral use.

9. A composition comprising:
0.5% carbomer (poly acrylic acid);
0.15% sodium hyaluronate;
1% poloxamer (copolymers of ethylene oxide and propylene oxide);
2% *Oryza sativa* extract;
0.25% proline,
0.25% glutamine and
0.25% hydroxyproline, wherein said percentages are by weight of the total weight (w/w).

* * * * *